United States Patent [19]
Zeldman et al.

[11] 3,948,274
[45] Apr. 6, 1976

[54] TRACHEAL TUBE WITH DISPOSABLE CANNULA
[75] Inventors: Maurice I. Zeldman, Pittsburgh; Gerald E. McGinnis, Monroeville, both of Pa.
[73] Assignee: Lanz Medical Products Corporation, Wilmerding, Pa.
[22] Filed: Jan. 20, 1975
[21] Appl. No.: 542,516

[52] U.S. Cl. .............................................. 128/351
[51] Int. Cl.² ....................................... A61M 16/00
[58] Field of Search ..................................... 128/351

[56] References Cited
UNITED STATES PATENTS
3,388,705  6/1968  Grosshandler ...................... 128/351
3,443,564  5/1969  Oehmig ............................... 128/351
3,599,642  8/1971  Tindel ................................. 128/351

Primary Examiner—Channing L. Pace
Attorney, Agent, or Firm—Brown, Murray, Flick & Peckham

[57] ABSTRACT

A tracheal tube having straight inner and outer end portions integrally connected by a curved central portion contains a cannula that can be removed from one end. The cannula is a normally straight one-piece flexible tube of plastic circumferentially corrugated from approximately its inner end outwardly to a point at least as far as the outer end of the curved central portion of the tracheal tube. The corrugated wall of the cannula stiffens the part of the cannula that extends through the curved central portion of the tracheal tube to prevent it from collapsing when the cannula is inserted in the tracheal tube.

5 Claims, 3 Drawing Figures

TRACHEAL TUBE WITH DISPOSABLE CANNULA

A tracheal tube is inserted into the trachea through an opening cut in the front of the throat. The tube typically has straight inner and outer end portions connected by a central curved portion or it may be formed entirely from an arc of a circle. The inner end portion extends down into the trachea, while the outer end portion extends out through the opening in the throat. The portion in the throat is generally encircled by an inflatable cuff to seal the space between the tube and the surrounding wall of the trachea so that all ventilation is through the tube. Tracheal tubes become obstructed by mucous and other secretions which collect and dry in them. Periodically removing the tubes for cleaning them and then reinserting them is highly objectional to the patient. It also requires a skilled person to do it.

It has, therefore, been proposed that another tube or cannula having a thin wall should be inserted in the tracheal tube so that this inner tube can be pulled out of the tracheal tube and cleaned or replaced by another cannula, all without disturbing the tracheal tube. The difficulty with using removable cannulas for this purpose is that if they are rigid, the entire tracheal tube must have a uniform radius from end to end and the cannula must have the same radius so that it can be inserted and removed. A tracheal tube of that shape is not desirable, because it lacks straight end portions for extending down in the trachea and straight forward from the throat. On the other hand, if a cannula is to be removed from a tracheal tube having straight end portions, the cannula must be flexible so that it can be inserted in the straight outer end portion of the tube and then pushed around the curved portion into the straight inner portion. An ordinary flexible tube, although it can be inserted in this manner, will collapse in the area extending through the curved portion of the tracheal tube. That will either restrict or close off the lumen.

An attempt to solve this problem is shown in U.S. Pat. No. 3,443,564, in which the portion of the cannula that has to pass around the curved portion of the tracheal tube is formed from a spirally wound wire. The convolutions of the wire normally are all close together to form a straight tube, but when the cannula is inserted in the outer end of the tracheal tube and pushed into it, the portions of the convolutions of the spiral wire at the inside of the curve will remain pressed together, but those at the outside of the curve will necessarily spread apart. Consequently, although the cannula will pass around the curve in the tracheal tube without collapsing, it does not have a solid side wall, but one containing numerous gaps between the convolutions of the wire.

Another objection to the cannula shown in the patent is that its construction is relatively expensive, so that it is not suitable as a disposable cannula. This means that it must be cleaned every time it is removed, which is not an easy task in view of the separate convolutions of the wire and the spiral grooves formed between them.

The patent also shows that the tracheal tube is tapered towards its inner end. This is done in order to facilitate insertion of the cannula, which also is tapered. If they are not tapered, it is extremely difficult to insert a wire cannula. The tapered tracheal tube also prevents any tendency of the convolutions at the inner end of the cannula to spread apart and hang down out of the tracheal tube.

Although the patent states that the disclosed cannula can be replaced by a flexible tube made of rubber or a synthetic material, it is presumed that the patentee meant that the rubber or synthetic material likewise should be in the form of a wound spiral. Otherwise, the suggestion in the patent is misleading because a solid wall tube formed from rubber or synthetic material would collapse in passing around the curved portion of the tracheal tube in the patent and thereby obstruct the tube.

It is an object of this invention to provide a cannula for insertion in a tracheal tube having straight inner and outer end portions, in which the cannula has a solid wall that is formed in such a manner that it will pass around the curve in the tracheal tube without collapsing. Other objects are to provide such a cannula which is so inexpensive that it is expendable, and which can be quickly and easily inserted in and removed from a tracheal tube by unskilled personnel.

The preferred embodiment of the invention is illustrated in the accompanying drawings, in which FIG. 1 is a side view, partly broken away in section, showing a tracheal tube containing our flexible cannula;

Figure 1:
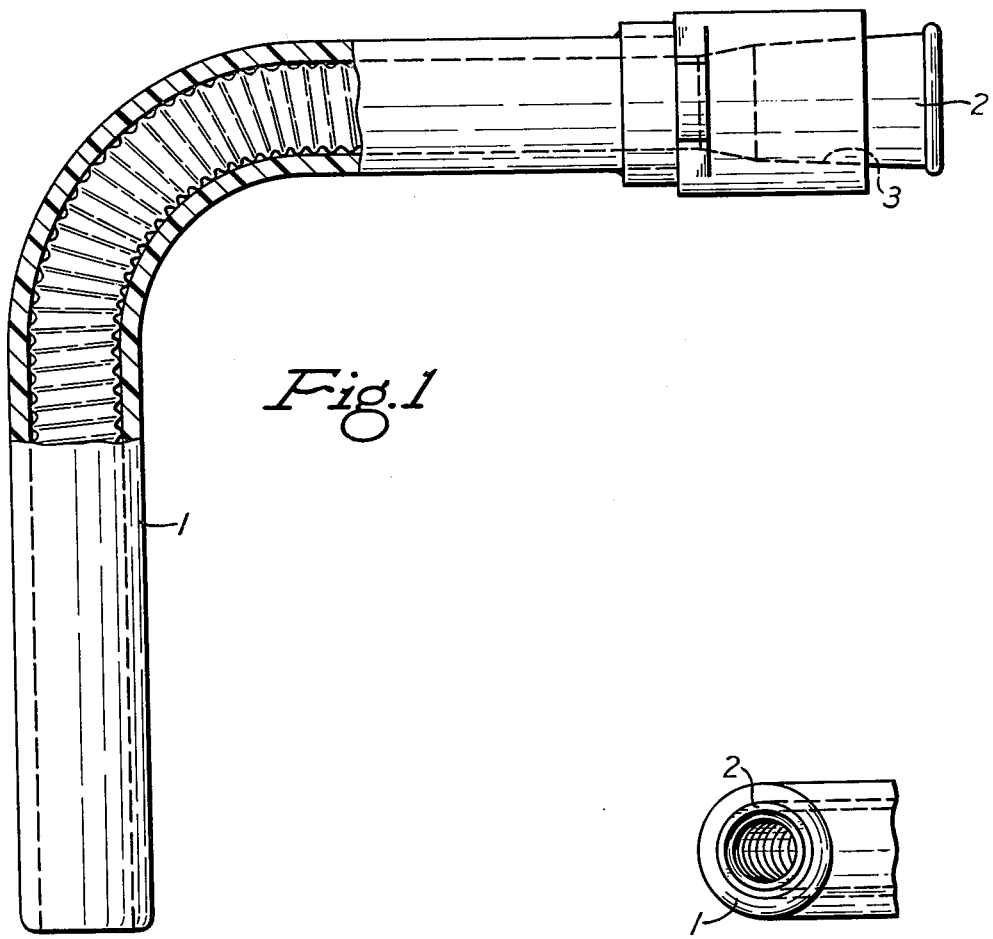
Figure 2:
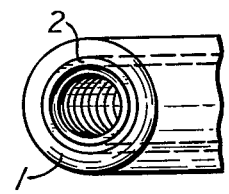
FIG. 2 is an end view of the distal ends of the two concentric tubes.

Referring to FIG. 1 of the drawings, a tracheal tube has substantially straight inner (lower) and outer (upper) end portions that are integrally connected by a curved central portion. This tube is inserted in a patient in the usual manner, with the outer or proximal end of the tube projecting from the front of his throat. The outer end portion is formed so that the tube can be held in place by a strap extending around the neck. The straight inner end portion of the tube may be provided with an inflatable cuff (not shown) to seal off the space between the tube and the surrounding wall of the trachea. This tube preferably is made of a suitable plastic or rubber and the straight end portions are disposed at an angle to each other between about 90° and 100°. The radius of curvature of the curved central portion of the tube has a length between about ⅝ inch and 1 ¼ inch. Tracheal tubes for children necessarily are shorter and have a shorter radius than those for adults. Also, the inner diameter of the tube can vary between about 5 mm and 10 mm, but for any given tube the inside diameter from its distal end to its proximal end or a point close to it preferably is uniform and not tapered.

Figure 3:
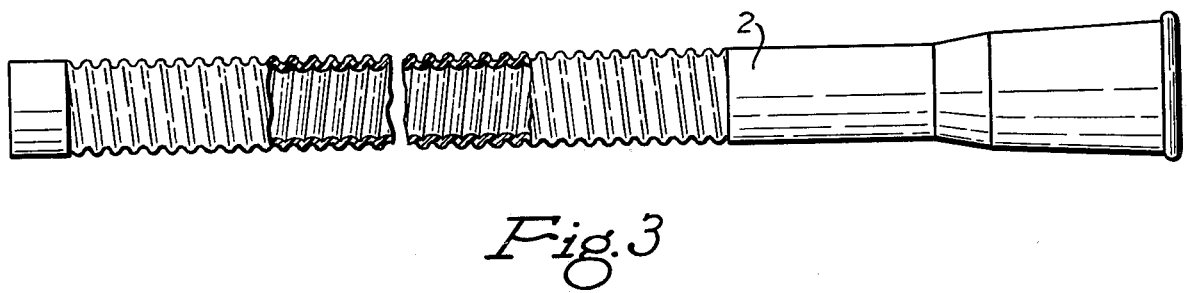
FIG. 3 is a side view of the cannula, partly in section, before insertion in the tracheal tube.

Disposed in this tracheal tube is a removable cannula that extends from end to end of the tracheal tube and preferably projects a short distance from its outer end so that it can be gripped easily in order to pull the cannula out of the tracheal tube. To limit the distance the cannula can be inserted in the outer tube, the outer end of the latter may be enlarged to provide a socket for an enlarged outer end of the cannula that fits in the socket. It is a feature of this invention that the cannula is a normally straight (FIG. 3) one-piece, flexible, tube made from a plastic and having a solid side wall that is less than 1 mm thick. Preferably, the wall is paper-thin, even less than ½ mm thick, so that the cannula will obstruct the passage through the tracheal tube as little as possible. The cannula engages the full circumference of the passage wall. If the cannula had a smooth plain wall throughout its length, it could be inserted in the tracheal tube but the portion of the cannula extending through the curved portion of the tracheal tube would be collapsed at one or more points because in order for the tube to curve lengthwise it would be necessary for its side wall at the inside of the curve to fold inwardly against the opposite side.

It is, therefore, another feature of this invention that the length of the cannula extending approximately from its inner end outwardly to a point at least as far as the outer end of the curved central portion of the tracheal tube is specially formed to prevent it from collapsing in passing through the curved central portion of the tracheal tube. This improvement in the cannula is accomplished by circumferentially corrugating the length of it just mentioned. The corrugations can be in the form of separate parallel rings integrally connected side by side or, as shown, they can be formed by a continuous helix. In either form, the wall of the cannula is similar to an accordian, in that the cannula can be stretched or compressed lengthwise to some extent and can be bent into a curve without collapsing because the portions of the corrugations at the inner side of the curve will be pressed closer together while the portions of the corrugations at the outer side of the curve will be stretched apart, as shown in FIG. 1. In fact, the cannula can even be bent into U-shape without collapsing, although, of course, that is not necessary but shows that there is not any danger of its collapsing in the curved portion of the tracheal tube, where it is bent no more than about 90°. The corrugations also stiffen the cannula radially, which aids in preventing collapsing. The short portion of the cannula between its enlarged outer end portion and the beginning of the corrugations does not need to be corrugated because it is not subjected to bending.

The cannula described herein is extremely inexpensive, so that when it is removed from a tracheal tube there is no reason to go to the trouble of cleaning it. It is simply discarded and a new one inserted in the tube. Since the side wall of the cannula can be paper thin, it does not reduce the inner diameter of the tracheal tube appreciably. Also, being formed from a suitable plastic, the cannula slides easily against the inner surface of the tracheal tube, especially if the latter also is made of a plastic. It takes only a couple of seconds to insert the cannula and no more than a second to remove it.

According to the provisions of the patent statutes, we have explained the principle of our invention and have illustrated and described what we now consider to represent its best embodiment. However, we desire to have it understood that, within the scope of the appended claims, the invention may be practiced otherwise than as specifically illustrated and described.

We claim:

1. The combination of a rigid tracheal tube having substantially straight inner and outer end portions integrally connected by a curved central portion that has a radius of curvature between about ⅝ inch and 1 ¼ inch long, and a disposable cannula fitting in said tube and extending from end to end thereof, said end portions of the tracheal tube being disposed at an angle to each other of between about 90° and 100°, and said cannula being a normally straight one-piece flexible tube formed of a plastic and having a solid wall less than 1 mm thick circumferentially corrugated from approximately its inner end outwardly to a point at least as far as the outer end of said curved central portion of the tracheal tube, said corrugated wall stiffening radially the length of cannula extending through said curved central portion of the tracheal tube and maintaining said length of cannula uncollapsed, the cannula being removable from the tracheal tube by pulling the outer end of the cannula.

2. The combination recited in claim 1, in which the tracheal tube from said outer end portion to the inner end of the tube has a substantially uniform diameter of between about 5 and 10 mm, and the corrugated length of the cannula is of substantially uniform size throughout its length to engage the inner surface of the tracheal tube.

3. An endotracheal device comprising a rigid tracheal tube having substantially straight inner and outer end portions integrally connected by a curved central portion that has a radius of curvature between about ⅝ inch and 1 ¼ inch long, said end portions of the tracheal tube being disposed at an angle to each other of between about 90° and 100°, the portions of said tube from its inner end to said outer end portion having a substantially uniform inner diameter of between about 5mm and 10mm, the inner diameter of said outer end portion being enlarged to provide a socket, and a disposable cannula fitting in said tube and extending from end to end thereof, said cannula being a normally straight one-piece flexible tube formed of a plastic and having a solid wall less than 1mm thick circumferentially corrugated from approximately its inner end outwardly to a point at least as far as the outer end of said curved central portion of the tracheal tube, the corrugated length of the cannula having a substantially uniform size throughout to engage the surrounding inner surface of the tracheal tube, said corrugated wall stiffening radially the length of cannula extending through said curved central portion of the tracheal tube and maintaining said length of cannula uncollapsed, and the outer end portion of the cannula being enlarged and smooth and uncorrugated and fitting in said socket, and the cannula being removable from the tracheal tube by pulling the outer end of the cannula.

4. The combination recited in claim 3, in which the tracheal tube from said socket to its inner end has a substantially uniform inside diameter, and the corrugated length of the cannula is of substantially uniform size throughout its length to engage the inner surface of the tracheal tube.

5. The combination recited in claim 4, in which the wall thickness of said cannula is less than ½ mm.

* * * * *